United States Patent
Lee

(10) Patent No.: US 8,012,762 B2
(45) Date of Patent: Sep. 6, 2011

(54) TEST DEVICE, AND RELATED METHODS

(76) Inventor: Steve Lee, Conway, AR (US)

( * ) Notice: Subject to any disclaimer, the term of this patent is extended or adjusted under 35 U.S.C. 154(b) by 242 days.

(21) Appl. No.: 12/082,982

(22) Filed: Apr. 16, 2008

(65) Prior Publication Data

US 2008/0286879 A1 Nov. 20, 2008

Related U.S. Application Data

(60) Provisional application No. 60/923,972, filed on Apr. 17, 2007.

(51) Int. Cl.
*G01N 21/77* (2006.01)

(52) U.S. Cl. ........ 436/169; 436/165; 436/168; 436/501; 436/512; 436/4; 436/7.1; 436/7.5; 436/7.92; 422/68.1; 422/69

(58) Field of Classification Search .................. None
See application file for complete search history.

(56) References Cited

U.S. PATENT DOCUMENTS 6,403,298 B1 * 6/2002 Lee et al. .................. 435/4

OTHER PUBLICATIONS

HowStuffWorks, Science Experiments for Kids, 2007, retrieved from internet::http://home.howstuffworks.com/science-experiments-for-kids.htm/printable.*

* cited by examiner

*Primary Examiner* — Yelena G. Gakh
*Assistant Examiner* — Robert Xu
(74) *Attorney, Agent, or Firm* — Lathrop & Gage LLP

(57) ABSTRACT

Test device for detection and visual indication of a specific analyte in a liquid sample such as a body fluid. The device includes a biodegradable housing, a test strip and a lid. The device is configured for placement in concentrate or dilute test liquid that is for example contained in a vessel. One end of the test strip wicks the liquid being tested into the housing and across a control site and test site which provide visual indication that the device is working correctly and whether the analyte being tested is present in the test liquid. An antibody specific to the antigen being tested may be provided on the test strip. The test device for example detects specific antigens in dilute urine, such that the device may be placed in a toilet bowl after urination.

21 Claims, 4 Drawing Sheets

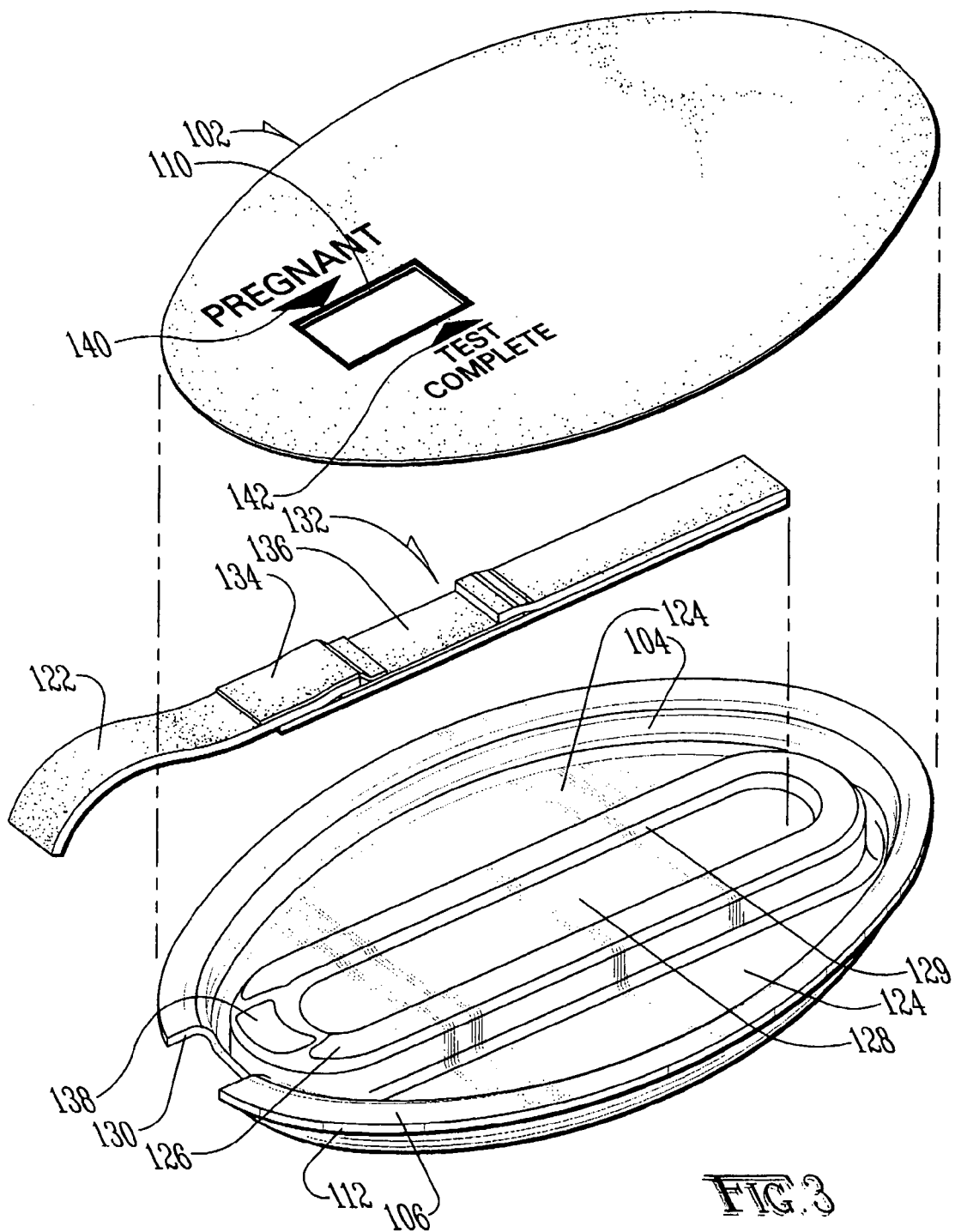

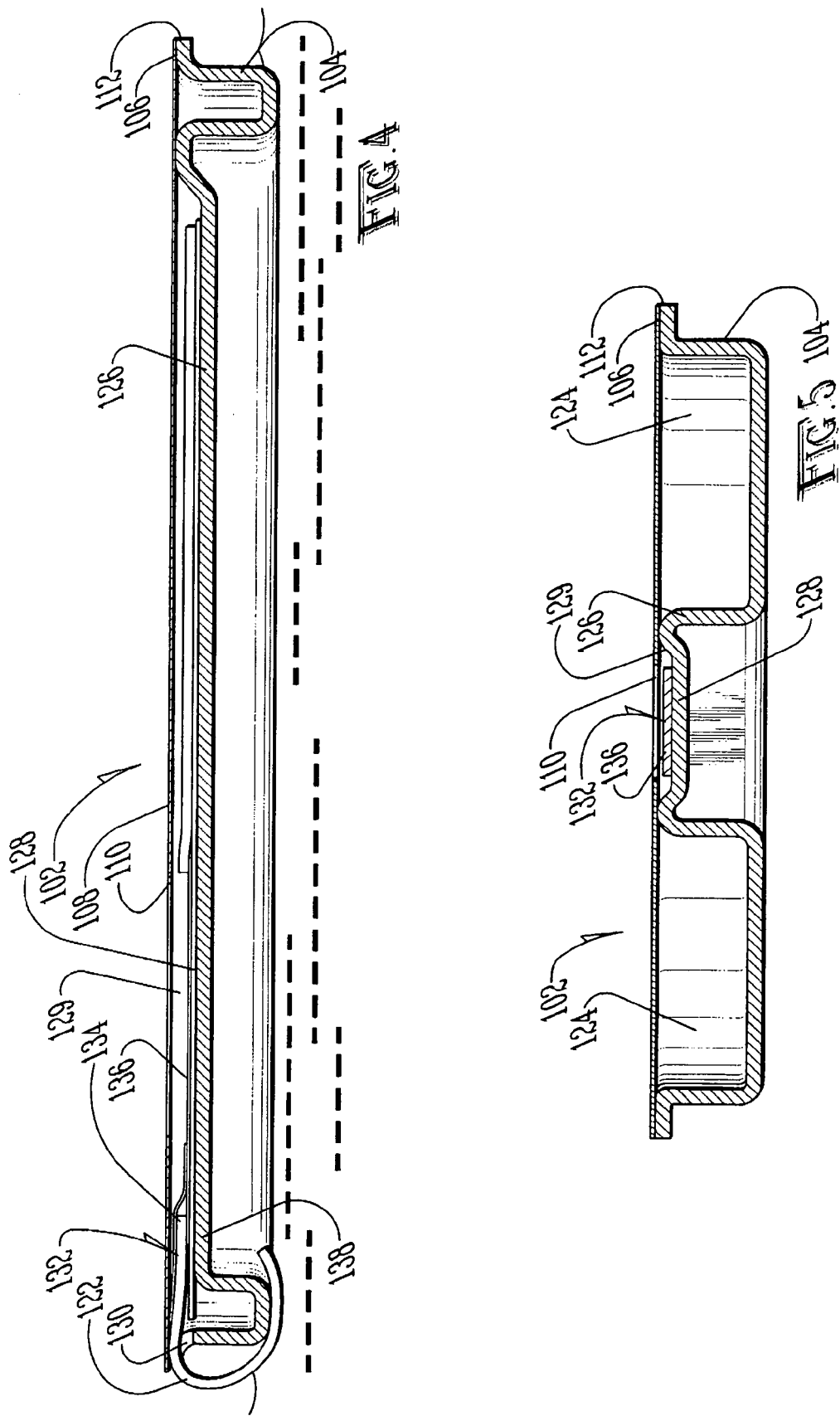

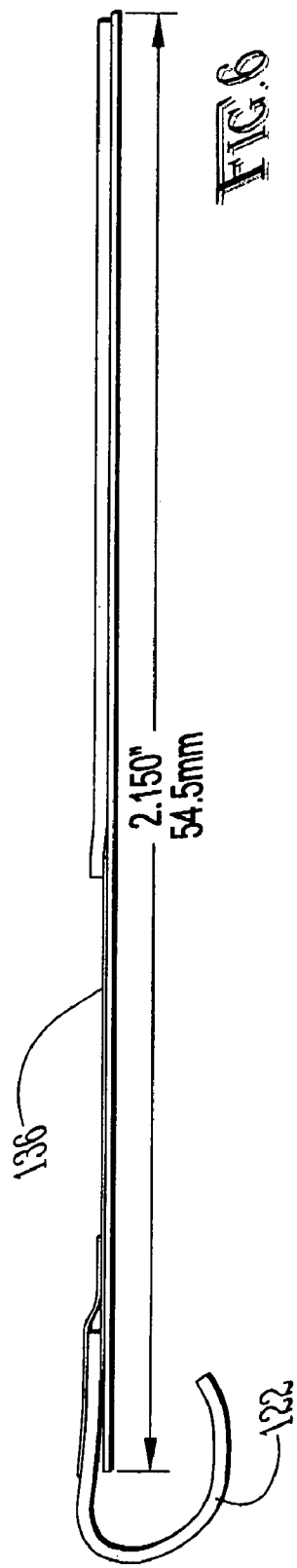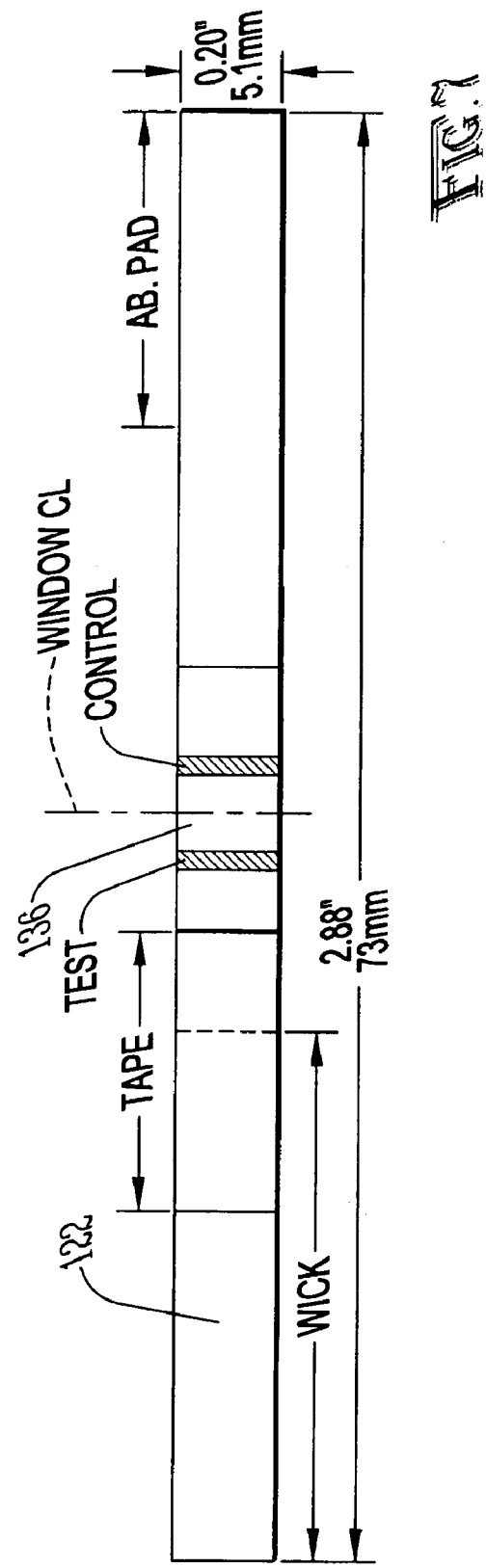

TEST DEVICE, AND RELATED METHODS

RELATED APPLICATION

This application claims the priority of Ser. No. 60/923,972 filed Apr. 17, 2007 and incorporates the disclosure of the referenced application herein.

BACKGROUND

This invention relates to a unique test device, more specifically a device for testing the presence of an anticipated analyte in liquid. Many devices are known to detect for the presence of a specific chemical, hormone or other material in liquid, such as blood, urine or even saliva. A variety of test devices are available which allow a user to test for the presence of HCG in urine, an early indicator of pregnancy, at home. Devices are also known for the detection of variety of chemicals, such as illegal drugs in urine, often associated with pre-employment or employment screenings. To date, such test devices have required the test subject to either urinate directly on the device, or to deposit urine in a receptacle and then position the device therein. This requirement is less than desirable and often results in a user coming in direct contact with their own urine, or in some instances coming into contact with the urine of a test subject.

SUMMARY

The disclosed test device is detects the presence of one or more analytes in a liquid sample, for example, human chorionic gonadotropin (HCG) in dilute urine. The disclosed test device is designed and constructed for use in dilute urine, concentrate urine or other test fluids. The disclosed device orients a test strip for determining and providing a visible indication of the presence or absence of an analyte, and is sufficiently buoyant to float on or near the surface of a volume of test fluid while facilitating contact between the strip and the fluid. Contact between the user and the test fluid may therefore be avoided.

The test device has a specifically configured housing. The housing is for example oval-shape; however, the housing may be formed in virtually any geometric shape, as a matter of design preference. The housing includes at least one bowl section, a peripheral edge and a rim at the upper-most peripheral edge. The rim is for example flat and substantially perpendicular to the periphery of the bowl. A plateau is formed within the bowl extending across substantially the width of the housing. The plateau is sized to accommodate a test strip containing an antibody specific to the analyte being tested for. The plateau may have a plurality of retention tabs or other fasteners to retain the test strip within the housing. Exemplary fasteners include water-resistant adhesives and Velcro® configured to mate with the strip or with one or more corresponding Velcro® strips or buttons on the strip. It is understood that any variety of adhesives may be used to fasten the strip to the housing.

The test strip includes a preselected reagent, specific to a target test substance or analyte, disposed between first and second ends of the strip. The reagent is for example layered onto the upper most surface of the strip in a specific design or pattern, such that the design or pattern appears when the intended analyte is detected. A test assurance or control strip may be disposed substantially adjacent the reagent which visually identifies whether the test strip is functioning by providing a visual indicator that test liquid has been absorbed and wicked to the reagent site. In one aspect, the first end of the test strip is disposed outside the housing so that it may directly contact the liquid into which the test device is placed. An opening may be provided through the sidewall of the bowl with the first end of the test strip protruding therethrough. The first end of the test strip is bent generally downward and is fixed to the outer surface of the housing substantially near the bottom of the housing.

In one embodiment, a test device includes a bowl-shaped housing with a peripheral rim. A plateau extends from an inner, bottom surface of the housing, for supporting a test strip within the housing. The test strip includes a reagent for reacting to a preselected analyte. A lid fastens to the peripheral rim, to cover the bowl; and a view port in the lid, overlies and aligns with the test strip. A test liquid contacting the test strip exposes the reagent to the analyte, when the test device is placed in the test liquid. Many test strips currently available on the market can be sized and configured for the housing. The strip is sized to the plateau, an extended wick at the first end is positioned through the housing and the strip sensitivity is enhanced by increasing the concentration of the reagent.

In one embodiment, a testing device for determining the presence of an analyte in liquid has a housing with a bowl section and a rim extending from the periphery of the bowl section. A plateau oriented through the bowl section supports a test strip. The test strip includes a reagent for reacting to the analyte. A lid fastens with the rim to cover the bowl section; and a view port in the lid aligns with the test strip. The test device floats and self-rights to display the view port to a user when placed in a vessel of test liquid, and the test liquid wicks onto the test strip to expose the reagent to the test liquid.

In one embodiment, a method of testing for an analyte in liquid, includes providing a bowl-shaped housing and securing a test strip within the bowl shaped housing. The test strip includes a reagent selected to react to the analyte, and is configured to generate a visual indicator when the reagent reacts to the analyte. A lid is affixed to the bowl-shaped housing, to at least partially enclose the test strip. A wicking mechanism is provided between the test strip and the environment external to the bowl, and the housing is floated in a test liquid. The test strip is viewed through a view port in the lid, to determine the presence of the analyte.

BRIEF DESCRIPTION OF THE DRAWINGS

FIG. 3 is a partially exploded plan view of the device of FIGS. 1 and 2, showing details of an embodied test strip.

FIG. 4 is a cross-sectional view of the test device of FIGS. 1-3, taken along lines 4-4 of FIG. 1 and illustrating details of the test strip of FIG. 3.

FIG. 5 is a cross-sectional view of the test device of FIGS. 1-3, taken along lines 5-5 of FIG. 1 and showing further details of the test strip of FIGS. 3 and 4.

FIG. 6 is a side plan view of the test strip of FIGS. 3-5.

FIG. 7 is a partial top plan view of the test strip of FIGS. 3-5.

DETAILED DESCRIPTION OF PREFERRED EMBODIMENTS

Figure 1:
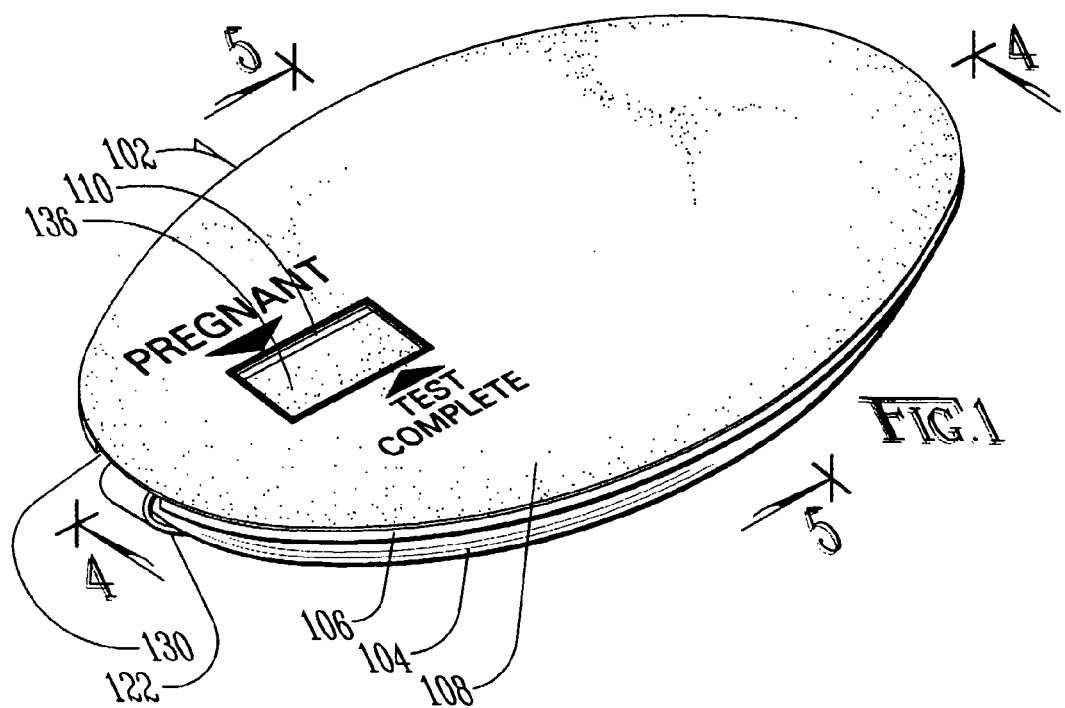
FIG. 1 is a top perspective view of a test device in accordance an embodiment.
Figure 2:
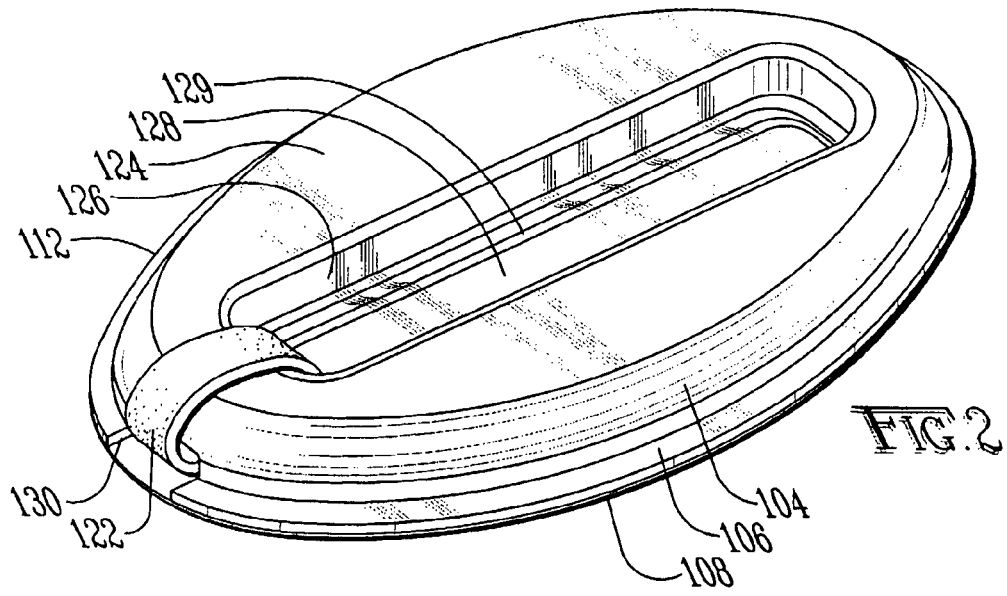
FIG. 2 is a bottom perspective view of the test device of FIG. 1.

Referring now generally to FIG. 1 through 3 of the drawings, there is shown a test device 102 for conducting an immunoassay to detect the presence of a specific antigen in a liquid sample of body fluid and to provide a visual indicator representative of the antigen in the fluid. Test device 102 for example detects an antigen, or ligand, in dilute urine and displays an visual indicator using a reagent that is a conjugate of reactive color particles and an antibody specific to the test antigen.

Device 102 is for example an antigen/receptor assay which can be used to detect the presence of various substances, often called ligands, in body fluids such as urine. Generally, such devices are found in home testing or clinical testing devices, for example, pregnancy detection systems or apparatus for the detection of illegal drugs in the urine. Such assays may involve an antigen/antibody reaction wherein a synthetic conjugate provides a visible tag. A specific antibody is provided specific to the antigen being detected. An absorbable indicator is provided, generally providing a simple positive/negative indicator for the presence of the antigen being detected. Many test strips are commercially available and with minor modification can be effectively used in the device.

Test device 102 includes a housing 104. Housing 104 is for example elliptical or oval in shape; however, it will be appreciated that housing 104 may be provided in a wide variety of shapes, e.g., as a matter of design preference or intended application. Housing 104 may be constructed of synthetic or natural materials, such as plastics , paper fiber, paper pulp products, cardboard, resins, natural fibers or combinations thereof. In one embodiment, housing 104 is a biodegradable material (or combination of biodegradable materials) that maintains its structural stability for a predetermined period of time, preferably between three and ten minutes, when subjected to a liquid sample before it begins to degrade. In one embodiment, the test device includes an oval shaped housing having a length of between two and five inches. The housing is manufactured from a paper fiber that begins to degrade within two minutes of being subjected to a liquid.

Housing 104 includes a lip 106 about its uppermost periphery. Lip 106 extends substantially perpendicularly from a side wall between $\frac{1}{32}$ and $\frac{1}{2}$ inches of housing 104 and provides a generally flat surface onto which a lid 108 can be positioned and fastened. Like housing 104, lid 108 may be made from a paper fiber or another biodegradable. Any variety of adhesives can be used to secure lid 108 to the lip 106 of housing 104. The overall geometric shape of the lid 108 is for example compatible with the general geometric shape of housing 104, such that lid 108 securely mates with and overlies lip 106. Lid 108 covers substantially an entire upper surface of housing 104, including part or all of lip 106. In addition to or in place of adhesive, lid 108 may snap or screw on to housing 104, e.g., connecting with lip 106. Lid 108 may also include a test opening for accommodating a portion of a test strip held within housing 104. The test opening aligns with both the control strip and a test reagent disposed with or impregnated into the a portion of the control strip.

A variety of materials may be used to make the different components of test device 102. In one embodiment, housing 104 is manufactured of a fiber board or paper composition, lid 108 is made of paper and a nonvolatile adhesive such as polyvinyl acetate is used to adhere lid 108 to lip 106.

A view port 110 in lid 108 provides a window into housing 104, for example over a plateau supporting a test strip or over an active and optionally, a control portion of the test strip. In one embodiment, a generally flat bottom section 124 of housing 104 has a raised surface or plateau 126 (resembling a trough when bottom section 124 is upside-down) which is for example created by press molding a portion of the housing bottom surface 124 generally upward as shown in FIGS. 3 and 5. As shown in FIGS. 3-5, plateau 126 may substantially bisect (e.g., be positioned along a midline of) bottom surface 124. A test strip 132 mounts within housing 104, in particular, within a depression 128, defined by wall 129, in plateau 126 that is viewable through port 110. The test strip 132 may be fastened into the depression 128 of the plateau 126 with an adhesive, or strip 132 may be mechanically secured within depression 128—for example, plateau 126 may include with one or more fasteners 130 which mechanically secure the test strip 132 in place. Fasteners 130 are for example tabs or hook and loop fasteners designed to mate with corresponding fasteners on test strip 132.

The overall shape of housing 104 encourages device 102 to self-right and to float when device 102 is placed or dropped in a liquid, such that port 110 and any underlying test strip 132 are viewable from above. When assembled with lid 108 secured, housing 104 may resemble a covered bowl. The larger diameter of lid 108 and the additional surface area provided by extending lip 106 for example contribute to buoyancy and self-righting. The plateau 126 elevates the test strip 132 above the test liquid during use which eliminates the possibility of the test strip 132 absorbing liquid directly through the housing 104 material.

Test device 102 is for example designed to test for the presence of HCG, or another analyte, in dilute urine in a toilet bowl. After the user urinates into a standard toilet bowl, test device 102 is placed in the dilute urine. Device 102 self-rights and floats on or near the surface of the dilute liquid. Accordingly, the user does not have to be careful when placing the device in the toilet to ensure a specific orientation. The device will self-right and float on the surface of the liquid to allow the user to visibly identify the test results which will be shown at the top of the device. It is understood that the device could also be used in concentrate urine, or other liquids, placed in a suitable receptacle.

In one aspect, device 102 provides for convenient and sanitary home pregnancy testing. A user simply urinates in a toilet in a customary fashion and is not subjected to the conventional problems of currently available pregnancy test devices, namely, coming into direct contact with the urine and disposing of a urine laden device. Test strip 132 provides a visual indicator that can clearly be read from several feet away so that the user can easily and clearly view the test results in the toilet bowl from a standing position.

Device 102 may be manufactured primarily or completely of biodegradable materials suitable for flushing into a sewer or septic system. This allows a user not desiring to keep a pregnancy test device to sanitarily dispose of the device by simply flushing the toilet once the results of testing are displayed, e.g., through via port 110 on test strip 132.

As shown in FIGS. 3 and 4, a first end 122 of test strip 132 extends from housing 104 to engage a test liquid. In one embodiment, first end 122 extends from housing 104 via a notch 130 formed through or adjacent to lip 106. Notch 130 is for example aligned with trough 126, such that a test strip 132 may be positioned along plateau 126 and depression 128 to extend from notch 130 (at end 122) without significant bending or twisting. Lid 108 is then twisted, pressed, adhered or otherwise secured to lip 106, to further retain test strip 132 in place. When secured to housing 104, lid 108 prevents undesirable splashing of liquid onto the test strip 132, e.g., when device 102 is placed or dropped in a test liquid. First end 122 may be wrapped around the outer surface of the housing 104 as shown in FIG. 2, to ensure that the test strip 132 is quickly exposed to the test liquid when device 102 is placed therein. First end 122 may be secured in place with an adhesive, a hook-and-loop fastener such as Velcro®, tabs or other fasteners that maintain its orientation and configuration.

In one example, first end 122 traverses up an inner wall of bowl-shaped housing 104, across lip 106 and through a notch 130 in lid 108. First end 122 is then bent downward and affixed to the outer surface of the housing such that the terminus of first end 122 lies generally below the bottom-most surface of the housing. This orientation ensures that first end 122 of test strip 132 comes into contact with the test liquid immediately upon device 102 being placed into or self-righting within the liquid. The test liquid is absorbed into first end 122 and wicks generally along the length of test strip 132 until it contacts first a control site 134 and then a test reagent at test site 136. Control site 134 provides a visual indicator that the test device is working appropriately, e.g., upon contact with the liquid wicked into strip 132. From control site 134, the test liquid continues to wick across test site 136, which is provided with an antibody that reacts to the presence of a selected antigen. For example, human chorionic gonadotropin (HCG) is an antigen that will be present in the urine of a pregnant woman. Several antibodies are known to react to the presence of HCG. These antibodies may be provided with a tag (e.g., colored particles or a dye) that visually indicates an antigen/antibody response when the chosen antibody contacts HCG present in urine.

It is understood that virtually any commercially available test strip can be configured to work in the inventive device. A test strip, such as those manufactured by Inverness under various trade names through various retailers can be utilized. The selected strip is re-configured for use in dilute urine and specifically within the inventive device. The first end 122 is elongated and positioned outside the housing 104 through the provided notch 130. It is preferred to increase the concentration of the reagent above levels commonly found in available test strips. The reagent concentration is preferably from between about 10 MIU (Milli International Units) and 30 MIU.

FIG. 3 depicts first end 122 extending through a port or hole 138 in the bottom 124 of housing 104. In one embodiment, port 138 extends through an end of plateau 126, such that the end 122 of a test strip 132 supported on plateau 126 drapes through port 138 to extend downward from housing 104, when device 102 floats (e.g., when device 102 self-rights) in a liquid. As described above, first end 122 may be secured to the outer surface of housing 104 with an adhesive or mechanical fastener.

In many situations (e.g., a possibly expectant mother undergoing a pregnancy test) rapid and sensitive detection of a test antigen is highly desirable. Device 102 may be specifically configured for use in dilute urine, with very sensitive antibodies on or in test area 136. A highly sensitive test area 136 for example insures detection of very low levels of antigens, as may be encountered in dilute urine.

FIG. 6 shows a test strip 132 with a backing material 150. Backing material 150 is provided and is generally formed from a non-porous polymer such as polyester. A membrane 152 overlies the backing 150 and is for example made from a porous nitrocellulose polymer. The first end 122, hereinafter also referred to as wick 122, is made from any wicking substance that absorbs the test liquid, such as woven mesh fibers or cellulosic filters. Test site 136 is for example a conjugate pad is for example a non-woven filter of glass, cellulose, polyester, plastic or any combination thereof; doped, coated or impregnated with an antibody specific to the intended test antigen. As shown in FIG. 7, a second end 157 of test strip 132 has an absorbent pad 158 provided in opposition to wick 122, to facilitate conduction of the test liquid along the length of test strip 132.

Since certain changes may be made in the above test device and methods without departing from the scope hereof, it is intended that all matter contained in the above description or shown in the accompanying drawings be interpreted as illustrative and not in a limiting sense. For example, the test device may be disposable or flushable. The test device may likewise be manufactured with test strips reactive to antigens not specifically recited above. The test device may also include a test strip impregnated or coated with chemicals that react to the presence of one or more drugs in a test fluid. Furthermore, the test device may react proportional to a level or amount of a test substance within a test fluid. The test device may accordingly indicate the sensed level or amount of test substance, which is for example useful in monitoring patient compliance with a drug regimen.

It is also to be understood that the following claims are to cover generic and specific features described herein, and all statements of the scope of the invention which, as a matter of language, might be said to fall there between.

What is claimed is:

1. A test device comprising:
a bowl-shaped housing with a peripheral rim;
a plateau extending from an inner, bottom surface of the housing and having a recessed area for supporting a test strip within the housing; the test strip comprising a reagent for reacting to a preselected analyte;
a lid for fastening to the peripheral rim, to cover the bowl;
an opening through the housing adjacent a first end of the test strip;
a wicking device extending through the opening and connected to the first end of the test strip; and
a view port in the lid, overlying and aligned with the test strip;
wherein a test liquid contacting the test strip exposes the reagent to the analyte, when the test device is placed in the test liquid, the wicking device engaging the liquid and wicking the liquid through the opening and onto the test strip; the plateau elevates the test strip above the test liquid to eliminate the possibility of the test strip absorbing the liquid directly through the housing.

2. The test device of claim 1, the test device comprising a pregnancy test device.

3. The test device of claim 2, the analyte comprising HCG in dilute urine, the reagent comprising an antibody reactive to HCG.

4. The test device of claim 3, the antibody tagged with an indicator for indicating the presence of HCG.

5. The test device of claim 1, the opening comprising a notch in the housing through which the first end of the test strip extends to engage the test liquid.

6. The test device of claim 5, further comprising one or more fasteners for holding the test strip in place.

7. The test device of claim 6, the one or more fasteners selected from the group of adhesives, tabs and hook-and-loop fasteners.

8. The test device of claim 1, wherein the housing, the test strip and the lid are biodegradable.

9. The test device of claim 1, wherein the housing, the test strip and the lid are flushable.

10. The test device of claim 1, one or both of the housing and the lid comprising paper fiber.

11. A testing device for determining the presence of an analyte in liquid, comprising:
a housing having a bowl section, a rim extending from the periphery of the bowl section;

a plateau oriented through the bowl section for supporting a test strip, the test strip including a reagent for reacting to the analyte;

a lid for fastening to the rim to cover the bowl section;

an opening through the housing adjacent a first end of the test strip;

the first end of the test strip extending through the opening, the first end of the test strip being bent generally downward and wrapped around the housing, the first end secured near an outer bottom surface of the housing; and a view port in the lid and aligned with the test strip;

wherein the test device floats and self-rights to display the view port to a user when placed in a vessel of test liquid and the first end of the test strip wicks the test liquid onto the test strip to expose the reagent to the test liquid; the plateau elevates the test strip above the test liquid to eliminate the possibility of the test strip absorbing the liquid directly through the housing.

12. The test device of claim 11, wherein the reagent reacts with HCG in urine, to generate a visual indicator representing the presence of HCG in the urine.

13. The test device of claim 12, the visual indicator appearing on a test area of the test strip viewable through the view port, when the urine contains HCG.

14. The test device of claim 12 wherein the urine is dilute.

15. The test device of claim 11, wherein the housing and the lid are elliptical in shape.

16. The test device of claim 11, wherein the housing and lid are oval-shaped.

17. The test device of claim 11, the housing and lid comprising biodegradable materials.

18. The test device of claim 11, further comprising at least one retention tab configured with the plateau, for securing the test strip in place.

19. The test device of claim 11, the analyte comprising a controlled substance, wherein the reagent reacts to the controlled substance to generate a visual indicator of the presence of the controlled substance in the liquid.

20. The test device of claim 19, wherein a test area of the test strip viewable through the view port includes the reagent.

21. The test device of claim 19, the visual indicator representing a level or amount of controlled substance in the liquid.

* * * * *